United States Patent
Monnier et al.

(10) Patent No.: US 6,388,106 B1
(45) Date of Patent: May 14, 2002

(54) SELECTIVE EPOXIDATION OF CONJUGATED DIOLEFINS

(75) Inventors: John Robert Monnier, Kingsport; Kimberly Thornton Peters, Piney Flats, both of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/864,582

(22) Filed: May 24, 2001

(51) Int. Cl.$^7$ ............................................. C07D 301/10
(52) U.S. Cl. ..................... 549/536; 549/534; 549/537
(58) Field of Search ................................. 549/534, 536, 549/537

(56) References Cited

U.S. PATENT DOCUMENTS

| | | |
|---|---|---|
| 2,879,276 A | 3/1959 | Mayo |
| 4,039,561 A | 8/1977 | Mitsuhata et al. |
| 4,140,690 A | 2/1979 | Dolhyj et al. |
| 4,169,009 A | 9/1979 | Wagner et al. |
| 4,267,073 A | 5/1981 | Nielsen et al. |
| 4,389,338 A | 6/1983 | Mitsuhata et al. |
| 4,390,738 A | 6/1983 | Waddan et al. |
| 4,420,625 A | 12/1983 | Sanderson et al. |
| 4,769,358 A | 9/1988 | Kishimoto et al. |
| 4,822,900 A | 4/1989 | Hayden |
| 4,883,889 A | 11/1989 | Pennington |
| 4,897,498 A | 1/1990 | Monnier et al. |
| 4,950,773 A | 8/1990 | Monnier et al. |
| 5,081,096 A | 1/1992 | Monnier et al. |
| 5,117,012 A | 5/1992 | Stavinoha et al. |
| 5,138,077 A | 8/1992 | Monnier et al. |
| 5,145,968 A | 9/1992 | Monnier et al. |
| 5,362,890 A | 11/1994 | Stavinoha et al. |
| 5,703,254 A | 12/1997 | Gaffney et al. |
| 5,770,746 A | 6/1998 | Cooker et al. |
| 5,780,657 A | 7/1998 | Cooker et al. |
| 6,011,163 A | 1/2000 | Barnicki et al. |

FOREIGN PATENT DOCUMENTS

| | | |
|---|---|---|
| CA | 527175 | 7/1956 |

OTHER PUBLICATIONS

Morrison et al, Organic Chemistry, Allyn and Bacon, Inc., Boston, 1959, pp. 154–155.
Brunauer et al, J. Am. Chem. Soc., 60, 1938, pp. 309–316.

*Primary Examiner*—Ba K. Trinh
(74) *Attorney, Agent, or Firm*—Michael J. Blake; Bernard J. Graves, Jr.

(57) ABSTRACT

Disclosed is a process for the preparation of mono-epoxides of certain diolefins wherein a conjugated diolefin, or polyolefin, that contains allylic carbon-hydrogen bonds, is contacted with molecular oxygen in the presence of a modified silver catalyst.

5 Claims, No Drawings

SELECTIVE EPOXIDATION OF CONJUGATED DIOLEFINS

FIELD OF THE INVENTION

This invention pertains to a gas phase process for the selective epoxidation of conjugated diolefins, or polyolefins, that contain allylic carbon-hydrogen bonds. More specifically, this invention pertains to the preparation of mono-epoxides by contacting in the gas phase a conjugated diolefin, or polyolefin, that contains allylic carbon-hydrogen bonds with molecular oxygen in the presence of a modified silver catalyst.

BACKGROUND OF THE INVENTION

Processes for the selective epoxidation of olefins which contain no allylic hydrogen atoms (non-allylic olefins) or olefins which contain hindered allylic hydrogen atoms are described by Monnier and Muehlbauer in U.S. Pat. Nos. 4,897,498, 4,950,773, 5,081,096, 5,138,077 and 5,145,968. Stavinoha and Tolleson disclose in U.S. Pat. No. 5,117,012 the selective epoxidation of 1,3-butadiene to 3,4-epoxy-1-butene (EpB) by contacting a mixture comprising 1,3-butadiene, oxygen and methane with a supported silver catalyst at elevated temperatures. Similarly, Stavinoha et al. U.S. Pat. No. 5,362,890 disclose a continuous process for the preparation of the monoepoxide of an olefin reactant selected from norbornene, norbornadiene and olefins having the general formula

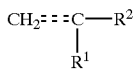

wherein $R^1$ is hydrogen or alkyl and $R^2$ is an aryl radical or the group

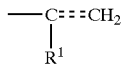

provided that the olefin reactants contain more than 2 carbon atoms and do not contain any allylic hydrogen atoms, by the steps of:

(1) continuously feeding a gas comprising about 3 to 30 mole percent of said olefin reactant, about 3 to 30 mole percent oxygen and about 40 to 90 mole percent of a paraffin hydrocarbon containing 2 to 6 carbon atoms wherein the oxygen:paraffin hydrocarbon mole ratio is in the range of about 0.03:1 to 0.75:1 to an epoxidation zone containing a supported, silver epoxidation catalyst and maintained at a temperature of about 175 to 230° C.; and (2) continuously removing from the epoxidation zone a gas comprising about 0.5 to 3.5 mole percent of said monoepoxide of the olefin reactant, about 2 to 28 mole percent of said olefin reactant, about 2 to 28 mole percent oxygen and about 40 to 90 mole percent of said paraffin hydrocarbon.

U.S. Pat. No. 6,011,163 describes a process for the preparation of the monoepoxide of an olefin reactant selected from norbornene, norbornadiene and olefins having the general formula

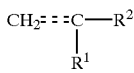

wherein $R^1$ is hydrogen or alkyl and $R^2$ is an aryl radical or the group

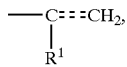

provided that the olefin reactants contain more than 2 carbon atoms and do not contain any allylic hydrogen atoms. The process comprises contacting norbornene, norbornadiene and olefins of formula (I) with molecular oxygen in the presence of a modified silver catalyst at elevated temperature and pressure. U.S. Pat. No. 4,897,498 discloses the epoxidation of 1,3-butadiene to produce 3,4-epoxy-1-butene as the selective reaction product. However, the same modified or promoted catalysts, or even unmodified silver catalysts, are essentially non-selective for the epoxidation of propylene to form propylene oxide. Attempted epoxidation yields only carbon dioxide and water as the reaction products. Propylene is the simplest example of an allylic olefin, which is defined in Morrison and Boyd, *Organic Chemistry,* Allyn and Bacon, Inc., Boston, 1959, pages 154–155, as an olefin containing hydrogen atoms attached to a carbon atom that is adjacent to a C=C double bond. Thus, propylene has one —$CH_3$ group (and three allylic hydrogen atoms) which is allylic to the C=C double bond of propylene, e.g., C=C—$CH_3$. On the other hand, olefins such as ethylene and 1,3-butadiene contain only vinylic hydrogen atoms that Morrison and Boyd define as hydrogen atoms that are attached to doubly-bonded carbon atoms, e.g., C=C—H. Furthermore, Morrison and Boyd state on page 155 that allylic hydrogen atoms are even easier to abstract than tertiary hydrogen atoms. In fact, Morrison and Boyd state that the reactivity sequence of hydrogen atoms can be written as

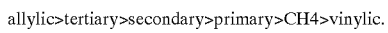

allylic>tertiary>secondary>primary>CH4>vinylic.

Furthermore, U.S. Pat. No. 5,770,746 discloses that the C—H bond energy of the allylic C—H bonds in propylene are 77 kcal/mole, while the C—H bond energy of the vinylic C—H bond in ethylene is 112 kcal/mole. Thus, it is readily apparent that abstraction of one of the allylic C—H bonds of propylene is preferable to addition of oxygen to the C=C double bond to form propylene oxide. Based on bond energetics alone, it is understandable why epoxidation of propylene, or any other allylic olefin, using molecular oxygen and promoted or unpromoted silver catalysts, results in non-selective oxidation, forming primarily carbon dioxide and water and little, if any, of the corresponding epoxide.

In view of the above stated relationships of olefin structure and reactivity, one would expect that the oxidation of any olefin which contains reactive allylic C—H bonds with molecular oxygen in the presence of a modified silver catalyst would not selectively produce an olefin epoxide. Thus, one skilled in the art would expect that the oxidation of conjugated diolefins such as isoprene (2-methyl-1,3-butadiene) or piperylene, (1,3-pentadiene), with molecular oxygen in the presence of a modified silver catalyst would not selectively produce an olefin epoxide, since each molecule contains a —$CH_3$ group which is allylic to a C=C double bond.

Epoxidation of conjugated diolefins containing allylic alkyl groups with allylic C—H bonds is described in U.S.

Pat. No. 2,879,276 using molecular oxygen in a liquid phase process. Accoding to this U.S. Pat. No. 2,879,276, no catalyst was necessary although in the presence of catalysts considered to be free radical initiators, such as azodiisobutyronitrile or benzoyl peroxide, the rates of olefin epoxide formation were higher. The oxygen concentrations in the process also were critical, and it was necessary to maintain oxygen concentrations between 0.1–40 mm (or torr) oxygen pressure, with oxygen concentrations of 3–6 mm being most preferable.

The epoxidation of propylene using very extensively modified silver catalysts is disclosed by Gaffney and coworkers in U.S. Pat. Nos. 5,703,254, 5,770,746, and 5,780,657. The catalyst compositions investigated by Gaffney comprised: 30–60% Ag, 0.5–3% K, 0.5–1% Cl, 0.5–2.5% Mo, 0.5–1% Re, 0.5–1% W, and balance $CaCO_3$. These catalyst were prepared by ball milling slurries of the components with powdered $CaCO_3$, thoroughly mixing the $CaCO_3$ with the other components. Thus, these catalyst compositions are not maintained on a support in the conventional sense of the term defined as supported catalysts.

Gaffney and coworkers demonstrated that the complex mixture of catalyst components and gas phase promoters was required for both activity and selectivity to propylene oxide. Thus, a catalyst composed of 50 weight percent Ag and 50 weight percent $CaCO_3$ gave only 3% selectivity to propylene oxide whereas a catalyst containing Ag, K, and $CaCO_3$ without any organic chloride or NO (nitric oxide) feed additive gave low conversion (<1%) and low selectivity (<3%). Co-feeding ethyl chloride and NO in the feedstream along with $C_3H_6$ and $O_2$ enhanced both conversion (up to 10%) and selectivity (up to 60%). The levels of ethyl chloride used with the Gaffney process (typically about 200 ppm) are many times higher than the levels typically used in the epoxidation of the olefins. Ordinarily, organic chloride levels higher than 10–50 ppm cause catalyst deactivation.

BRIEF SUMMARY OF THE INVENTION

We have discovered that certain conjugated diolefins that contain allylic carbon-hydrogen bonds may be selectively converted to olefin epoxides by contacting in the gas phase the conjugated diolefin containing allylic carbon-hydrogen bonds with molecular oxygen in the presence of a modified silver catalyst. The present invention therefore provides a process for the preparation of the monoepoxide of an olefin reactant having the formula:

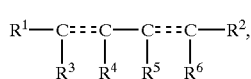
(I)

wherein $R^1$, $R^2$, $R^3$, $R^4$, $R^5$, and $R^6$ are independently selected from hydrogen, methyl, and $C_2$–$C_6$ linear or branched alkyl groups, provided that at least one $R^1$, $R^2$, $R^3$, $R^4$, $R^5$, and $R^6$ contains at least one C—H group that is allylic to one or both of the adjacent C=C double bonds, which comprises contacting the olefin reactant in the gas phase with an oxygen-containing gas in the presence of a supported silver catalyst at epoxide-forming conditions of pressure and temperature, wherein the catalyst comprises a catalyst support material having a surface area of less than 10 square meters per gram having distributed on the surface thereof about 1 to 30 weight percent silver and about 10 to 5000 parts per million by weight (ppmw) of an epoxidation catalyst modifier selected from alkali earth metals, alkaline earth metals and thallium.

DETAILED DESCRIPTION

The olefin reactants employed in the process of the present invention have the formula:

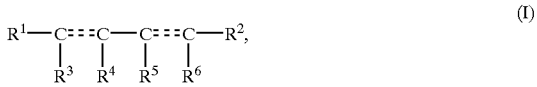

wherein $R^1$, $R^2$, $R^3$, $R^4$, $R^5$, and $R^6$ are independently selected from hydrogen, methyl, and $C_2$–$C_6$ linear or branched alkyl groups, provided that at least one $R^1$, $R^2$, $R^3$, $R^4$, $R^5$, and $R^6$ contains at least one C—H group that is allylic to one or both of the adjacent C=C double bonds. The olefin reactant contains at least 5 carbon atoms and typically not more than about 20 carbon atoms, preferably not more than about 12 carbon atoms. Specific examples of the olefin reactants include isoprene (2-methyl-1,3-butadiene) and piperylene (1,3-pentadiene). The epoxide product obtained from our novel process typically is a mixture of the two epoxide isomers, e.g., 3,4-epoxy-2-methyl-1-butene and 3,4-epoxy-3-methyl-1-butene from isoprene. Of the isomers, 3,4-epoxy-2-methyl-1-butene represents epoxidation of the C=C double bond, which does not contains the allylic —$CH_3$ group, while 3,4-epoxy-3-methyl-1-butene represents epoxidation of the C=C double bond, which does contain the allylic —$CH_3$ group in isoprene.

The supported silver epoxidation catalysts which may be used in the process provided by our invention are known materials which may be prepared according to published procedures including the catalyst manufacturing procedures described in U.S. Pat. Nos. 4,039,561, 4,169,009, 4,267,073, 4,389,338, 4,769,358 and 5,081,096. Thus, the catalysts useful in the present process comprise a catalyst support material having deposited on its surface about 1 to 30 weight percent silver and about 10 to 5000 parts per million by weight (ppmw) of an epoxidation catalyst modifier selected from alkali earth metals, alkaline earth metals and thallium. The weight percentage silver and ppmw modifier (also referred to as promoter) are based on the total weight of the catalyst, i.e., the finished catalyst. Although the modifier component of the catalyst may exist as a salt, oxide or hydroxide of the modifier element, the modifier concentration of the catalyst is based on modifier element alone.

The support component of the catalysts may be selected from the large number of conventional, porous, refractory catalyst carriers or support materials which are essentially inert in the presence of the ethylenically unsaturated compound and oxygen-containing gas feeds and the products in the processes in which the catalysts are employed. Such conventional materials may be of natural or synthetic origin and preferably are of a macroporous structure, that is, a structure having a surface area below about 10 $m^2/g$. These support materials typically have an apparent porosity of greater than 20%. Supports having a siliceous and/or aluminous composition are, in general, preferred. Specific examples of suitable supports are the aluminum oxides (including the materials sold under the trade name "Alundum"), pumice, magnesia, zirconia, kieselguhr, fuller's earth, silicon carbide, porous agglomerates comprising silicon and/or silicon carbide, silica, selected clays, artificial and natural zeolites and ceramics. Refractory supports particularly useful in the preparation of the catalysts useful in the process of our invention comprise the aluminous materials, in particular those containing alpha alumina. In the case of alpha alumina-containing supports, preference is given to those having a specific surface area as measured by the B.E.T. method of from about 0.03 to 10 m²/g and an apparent porosity as measured by conventional mercury or water absorption techniques of from about 25 to about 60% by volume. The B.E.T. method for determining specific surface area is described in detail in Brunauer, S., Emmett, P. H., and Teller, E., J. Am. Chem. Soc., 60, 309–16 (1938).

The following materials are specific examples of the catalyst supports which may be used.

I. Norton SN-06595, a fluidizable powder having a surface area of 0.26 m²/g, a total pore volume of 0.675 cc (Hg)/gm, median pore diameter 19 microns ($\mu$), a packing density of 0.98 g/cm³, and a chemical composition (weight percent) of: $Al_2O_3$—84.7, $SiO_2$—13.4, $Fe_2O_3$—0.21, $TiO_2$—0.47, CaO—0.21, MgO—0.12, $Na_2O$—0.15, $K_2O$—0.26).

II. Norton SN-08228, 0.1875 inch pellets with a surface area of 0.26 m²/g, a total pore volume of 0.23 cc(Hg)/gm, median pore diameter of 19$\mu$, a packing density of 0.90 g/cm³, and a chemical composition (weight percent) of: alumina—84.7, $SiO_2$—13.4, $Fe_2O_3$—0.21, $TiO_2$—0.47, CaO—0.21, MgO—0.12, $Na_2O$—0.15, $K_2O$—0.26.

II. Norton SA-5252, 0.1875 inch spheres with a surface area of 0.39 m²/g, a total pore volume of 0.36 cc(Hg)/gm, median pore diameter of 5.4$\mu$, a packing density of 0.94 g/cm³ and a chemical composition (weight percent) as follows: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

IV. Norton 5552 Alumina Rings—0.25 inch rings having a surface area of 0.43 m²/g, a total pore volume of 0.37 cc (Hg)/gm, a median pore diameter of 7$\mu$, a packing density of 0.80 g/cm³, and a chemical composition (weight percent) of: $Al_2O_3$—93.1, $SiO_2$—5.6, $Fe_2O_3$—0.3, $TiO_2$—0.1, CaO—0.1, MgO—0.3, $Na_2O$—0.1, $K_2O$—0.1.

V. Norton SN-82501, 0.1875 inch spheres having a surface area of 0.13 m²/g, a total pore volume of 0.37 cc(Hg)/gm, a median pore diameter of 32.5$\mu$, a packing density of 0.88 g/cm³, and a chemical composition (weight percent) of: $Al_2O_3$—85.0, $SiO_2$—12.0, and the remaining 3% as $Fe_2O_3$, $TiO_2$, CaO, MgO, $Na_2O$ and $K_2O$.

Although not preferred, other support materials which may be used include zinc oxide, e.g., having a surface area of about 3.9 m²/g and a particle size of about 75–250$\mu$; titania, e.g., having a surface area of about 0.5 m²/g and a particle size of about 40–75$\mu$; calcium oxide; silica, e.g., having a surface area of about 0.18 m²/g and a particle size of about 75–250$\mu$; barium oxide, e.g., having a surface area of about 1 m²/g and a particle size of 40–75$\mu$; boron nitride; silicon nitride; and silicon carbide.

A preferred class of support materials comprise low surface area, fused, alpha alumina supports which have relatively uniform pore diameters and are more fully characterized by having (1) B.E.T. specific surface areas of from about 0.1 m2/g to about 2.0 m²/g, preferably about 0.3 m²/g to about 1.0 m²/g, and (2) apparent porosities of from about 42% to about 60%, preferably from about 46% to about 58%.

The actual physical form of the catalyst support is not particularly important. While the form of the catalyst support has little effect on catalyst activity, practical considerations such as ease of heat transfer, mass transfer, pressure drop due to fluid flow restrictions, efficiency of gas-liquid—solid contacting, catalyst durability, and the like make the use of defined shapes such as spheres, pellets, extrudates, rings, saddles, and the like preferred. Conventional commercial fixed-bed reactors used in the epoxidation of ethylenically-unsaturated compounds typically are in the form of a plurality of parallel, or series of, elongated tubes (in a suitable shell). In such reactors, it is desirable to employ a support formed into a rounded shape, such as, for example, spheres, pellets, rings, tablets, and the like, having diameters of from about 0.1 inch to about 0.8 inch.

A preferred method of preparing the catalysts from an inorganic silver compound comprises the steps of (1) forming a catalyst precursor by contacting, in either one or two steps, a porous support material with aqueous solutions of an inorganic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) intimately contacting at a temperature of about 170 to 600° C. the catalyst precursor with a gas comprising (i) hydrogen or (ii) an inert gas containing at least 4 volume percent hydrogen. The preparation of the catalysts from an organic silver compound such as a silver amine oxalate, e.g., silver bis-ethylenediamine oxalate, comprises the steps of (1) forming a catalyst precursor by contacting, in either one or two steps, a porous support material with aqueous solutions of an organic silver compound and a modifier compound and drying the resulting impregnated support material, (2) optionally calcining the catalyst precursor wherein a gas such as air, oxygen-depleted air, nitrogen, argon, helium or the like is passed over or through the catalyst precursor at elevated temperatures, and (3) heating the catalyst precursor at a temperature of about 150 to 300° C. to thermally decompose the organic silver compound.

The catalyst precursors may be prepared employing techniques well known to those of skill in the art, such as, for example, by precipitation of suitable silver and modifier compounds on the support, by impregnation, by co-precipitation of the silver and modifier compounds and the support material, by grinding together the support material and the silver and modifier compounds in particulate form and the like. The order in which the modifier is incorporated onto the support material is not critical, e.g., the support may be contacted with a silver source, then the modifier, or the support may be contacted with the modifier compound, then a silver compound, or the support material may be contacted simultaneously with both a modifier compound and a silver compound.

The silver compound employed in the preparation of the catalyst precursor is not critical. Typically, the preparation of the catalyst precursor comprises impregnating the support material with a solution of a silver compound in water, an alcohol, a glycol ether, or a mixture thereof. Exemplary compounds are silver nitrate, silver oxalate, silver acetate, and the like. Those skilled in the art recognize that certain organic silver compounds require the addition of ammonia or an amine in order to solubilize the organic silver compound in an aqueous medium; thus, the use of such solvation-promoting additives is contemplated in the practice of the present invention.

The catalysts may contain about 1 to 30 weight percent silver, calculated as elemental or metallic silver and based on the total weight of active catalyst. The loading level of silver on the support preferably is within the range of about 2 up to 25 weight percent, most preferably about 5 to 20 weight percent, elemental silver. The silver typically is present in the form of uniformly-spaced, discontinuous, adherent, substantially hemispherical, discrete particles having an essentially uniform diameter of about 0.1 to 5.0$\mu$. Catalysts bearing silver particles less than about 0.1μ give inferior catalytic results whereas silver particles larger than about 5.0μ do not appear as uniformly-spaced, discontinuous particles but appear to give a continuous layer of inter-grown crystals which results in a catalyst having inferior activity due to loss of silver surface area.

The chemical form of the modifier component of the finished catalysts is not known. However, the heat and/or hydrogen treatment given to the impregnated support in the reduction of the silver salts to metallic silver most likely converts the modifier compounds or salts to an oxide, oxidic or halide compound. The amount of modifier compound present on the catalyst support is expressed herein as the weight percent, based on the total weight of the catalyst, of the modifier element rather than the modifier compound.

The amount of modifier element present on the catalyst surface may vary substantially depending, for example, on the particular support material employed and/or the surface area thereof and the amount of silver on the catalyst. Generally, the amount of modifier element on the active catalyst is in the range of about 10 to 5000 parts per million (ppm, by weight) based on the total weight of the active catalyst. The concentration of modifier preferably is in the range of about 20 to 3000 ppm with amounts in the range of about 50 to 1600 ppm (same basis) being especially preferred. The modifier element preferably is cesium, rubidium or thallium. Normally, the silver: modifier weight ratio of the finished or active catalysts is in the range of about 50:1 to 4000:1, preferably in the range of about 100:1 to 2500:1, and most preferably in the range of about 100:1 to 2000:1.

Silver and the modifier normally are the only active constituents which are added to the support materials in catalytically effective amounts. However, it is not unusual for substantial amounts, often up to about 10,000 ppm by weight of an alkali metal (usually potassium) to be present within the porous support due to (1) the use of support materials containing naturally occurring alkali metals or (2) the addition of alkali metal during support manufacture. These amounts of alkali metal are present in the support in non-leachable form, rather than on the surface and do not appear to contribute to the performance of the catalysts.

The catalyst precursor comprising a catalyst support material having the silver and modifier compounds deposited thereon as described herein above is converted to an active catalyst by intimately contacting the precursor, after the optional calcination step, with a gas comprising (i) hydrogen, or (ii) an inert gas containing at least about 4 volume percent hydrogen at a temperature of about 170 to 600° C. whereby the silver compound is reduced to elemental silver and the thallium metal compound is believed to be converted to an oxide and/or hydroxide. The particular conditions employed in the high temperature hydrogen treatment can vary substantially since the hydrogen concentration and temperature as well as contact times are interdependent. Alternatively, when the catalyst precursor comprises an organic silver compound, such as an amine-solubilized silver oxalate, the catalyst precursor may be converted to the active state by thermal decomposition in air at temperatures of about 150 to 300° C. Such thermal decomposition requires that the catalyst precursor be heated at a temperature and for a period of time sufficient to completely reduce the organic silver salt to metallic silver.

Our novel process may be carried out at a temperature in the range of about 175 to 250° C. with the range of 185 to 225° C. being particularly preferred. The pressure within the epoxidation zone may range from about 0.5 to 20 bar absolute (bara), preferably about 1 to 10 bara. It is apparent that the particular combination of temperature and pressure is selected so as to maintain all of the components of the feed to the epoxidation zone in the gaseous state. The inert diluent which may be used in the present process may be selected from helium, nitrogen, and paraffin hydrocarbons such as straight- or branched-chain alkanes containing up to about 6 carbon atoms, e.g., methane, ethane, propane, butane, isobutane, pentane and hexane.

The advantages and benefits provided by the present invention may be achieved by feeding to the epoxidation zone a gas comprising about 3 to 30 mole percent of said olefin reactant, about 3 to 30 mole percent oxygen and about 40 to 90 mole percent of an inert diluent gas such as nitrogen, argon, helium, or mixtures thereof, or a paraffin hydrocarbon containing 1 to 6 carbon atoms, or a mixture thereof, wherein the oxygen:diluent gas mole ratio is in the range of about 0.03:1 to 0.75:1. Optionally, about 2 to 2000 parts per million by volume (ppmv) of at least one nitrogen-containing basic compound may be included in the feed gas. The optional nitrogen-containing basic compound preferably is ammonia or a mono-, di-, or tri-alkylamine having a boiling point of less than about 150° C., more preferably ammonia or a mono- or di-alkylamine having a boiling point of less than about 150° C. containing up to about 12 carbon atoms, most preferably ammonia. The optional nitrogen-containing basic compound preferably is used in a concentration of about 20 to 500 ppmv. Normally, the feed gas also will contain a total of about 1 to 10 mole percent of other components such as water, carbon dioxide, argon and recycled epoxide product. Up to about 10 mole percent of the inert diluent component of the feed gas may be made up of one or more other inert gases such as such as argon, helium, and nitrogen. The feed gas to our novel continuous process preferably comprises (1) about 3 to 25 mole percent of the olefin reactant, (2) about 5 to 25 mole percent oxygen, (3) about 40 to 80 mole percent of a paraffin hydrocarbon containing 1 to 6 carbon atoms, (4) 20 to 500 ppmv ammonia and/or an amine, and (5) a total of about 0 to 10 mole percent of other components selected from water, carbon dioxide, argon and recycled epoxide product.

The selectivity of our novel epoxidation process may be increased by performing the process in the presence of halide, typically chloride, ion. Halide ion may be provided to the process by using a halide (chloride) salt of the modifier employed in the preparation of the catalysts. Alternatively, some or all of the halide ion may be provided to the process by including one or more organic halides in the gaseous feed, e.g., in a concentration of about 1 to 40 ppm. Examples of such organic halides include compounds having the formula $R^3X$ wherein $R^3$ is a hydrocarbyl group or a halogenated hydrocarbyl group containing up to about 8 carbon atoms and X is a halogen atom, preferably chloro or bromo, and wherein $R^3$ contains at least one hydrogen atom which is sufficiently acidic so as to render $R^3X$ capable of undergoing dehydrohalogenation under the reaction conditions. Exemplary organic halides include $C_1$ compounds such as methyl chloride, methyl bromide, methylene chloride, methylene bromide, chloroform and bromoform, and the like; $C_2$ compounds such as ethyl chloride, ethyl bromide, dichloroethane, dibromoethane, vinyl chloride, dichloroethylene, trichloroethylene, and the like; $C_3$ compounds such as dichloropropane, dibromopropane, dichloropropene, dibromopropene, and the like; $C_4$ compounds such as chlorobutane, bromobutane, dichlorobutane, dibromobutane, chlorobutene, bromobutene, dichlorobutene, dibromobutene, and the like; $C_5$ compounds such as mono-, di-, tri-, tetra-, and pentachloropentanes or pentenes, mono-, di-, tri-, tetra-, and pentabromopentanes or pentenes, cyclopentylchloride, cyclopentylbromide, and the like; $C_6$ compounds such as mono-, di-, tri-, tetra-, penta-, and hexachlorohexanes or hexenes, mono-, di-, tri-, tetra-, penta-, and hexabromohexanes or hexenes, cyclohexylchloride, cyclohexylbromide, chlorobenzene, bromobenzene, and the like; $C_7$ compounds such as chlorotoluene, bromotoluene, benzyl chloride, benzyl bromide, mono-, di-, tri-, tetra-, penta-, hexa-, and heptachloroheptanes or heptenes, mono-, di-, tri-, tetra-, penta-, hexa-, and heptabromoheptanes or heptenes, chlorocycloheptane, bromocycloheptane, and the like; $C_8$ compounds such as mono-, di-, tri-, tetra-, penta-, hexa-, hepta- and octachlorooctanes or octenes, mono-, di-, tri-, tetra-, penta-, hexa-, hepta-, and octabromooctanes or octenes, and the like; as well as mixtures of any two or more thereof. Dichloroethane, ethyl chloride, and chlorobutane are the preferred organic halides.

The organic halide can be added to the oxidation reaction zone in a variety of ways. For example, it can be mixed with the olefin to be oxidized and/or the oxygen-containing gas prior to contacting with the catalyst, or the organic halide can be introduced to the reaction zone separately from the feed olefin and/or the oxygen-containing gas. The concentration of the organic halide in the feed to the epoxidation zone may be in the range of about 1 to 100 parts per million volume (ppmv), preferably about 2 to 20 (ppmv).

EXAMPLES

The novel process of the present invention is further illustrated by the following examples. Unless stated otherwise, the epoxidation catalysts employed in the examples are comprised a fused α-alumina support in the form of particles having diameters ranging from 0.7 to 1 cm having deposited thereon 12–15 weight percent silver and variable parts per million by weight (ppmw) promoter salts selected from CsCl, $CsNO_3$, RbCl, and TlCl. These catalysts were prepared according to known procedures by impregnating the support material with solutions of a silver amine salt and promoter followed by a thermal decomposition/reduction treatment in the presence of an oxygen-containing gas to convert the silver salt to silver metal.

Catalyst performance was measured after steady state operation had been reached for each combination of process conditions. Catalytic activity is expressed as mole percent of epoxide (mole % epoxide) in the reactor effluent where mole % epoxide is defined as $$\frac{\text{Moles epoxide in product effluent}}{\text{Total moles of all gas components in product effluent}} \times 100$$

and selectivity is the percent selectivity to epoxide defined as $$\frac{\text{Moles feed olefin converted to epoxide}}{\text{Moles feed olefin converted to all products}} \times 100.$$

Catalytic activity also may be expressed as percent conversion of feed olefin in the feed stream, wherein percent conversion is defined as $$\frac{\text{Moles feed olefin converted to products}}{\text{Moles feed olefin fed}} \times 100$$

Comparative Example 1

Butadiene and propylene epoxidation reactions were carried out in a tubular Pyrex reactor containing catalyst charges of 3.0–3.2 grams in the mid-section of the tube. The catalyst bed dimensions were approximately 10 mm diameter×25 mm in height. Catalyst samples were ground and sieved to give particle diameters between 0.8–2.0 mm. The reactor was tightly clad with a 2.5 cm outside diameter aluminum jacket to help ensure a more isothermal catalyst bed. A thermocouple embedded in the catalyst bed was used to monitor and maintain catalyst temperature. Before reaction, the catalyst sample was loaded into the reactor and heated in flowing air in situ at 250° C. for 2 hours. The temperature of the sample was then lowered to 190° C. at which point the epoxidation of feed olefin/diolefin was then commenced by feeding to the reactor/catalyst a gaseous feed stream typically composed of 2–20% (molar) olefin/diolefin and 15–30% (molar) oxygen with the balance being n-butane plus 2 ppm (vol) of 2-chlorobutane as reaction moderator. Catalyst performance was monitored every two hours throughout the entire run by an in-line gas sampling loop that injected a gas sample into a Poraplot Q gas chromatographic column installed in an Hewlett-Packard 5890 Series Gas Chromatograph.

A catalyst containing 12 weight percent Ag supported on fused α-alumina support was promoted with 700 ppm Cs (the Cs was added as CsCl) and evaluated for catalytic activity for butadiene and propylene epoxidation at 1 bara overall pressure and 205° C. For butadiene epoxidation, the feed composition was 17% 1,3-butadiene, 17% oxygen, 66% n-butane diluent, and 2 ppm 2-chlorobutane. At a reaction temperature of 205° C. and a gas hourly space velocity (GHSV) of 6200 $hr^{-1}$, the conversion of butadiene ($C_4H_6$) was 16.1% and the selectivity to 3,4-epoxy-1-butene was 87.9%. The only other reaction products detected were $CO_2$ and $H_2O$.

The catalyst was then evaluated for propylene epoxidation by replacing the 1,3-butadiene feed with 12.8% propylene in the feed to give a feed composition of 12.8% propylene, 17% oxygen, 70.2% n-butane, and 2 ppm 2-chlorobutane. At a reaction temperature of 205° C. and a gas hourly space velocity (GHSV) of 6200 $hr^{-1}$, the conversion of propylene was 6.6% and the selectivity to propylene oxide was 2.6%, with the balance of the reaction products being $CO_2$ and $H_2O$.

Thus, the catalyst gave the performance expected for epoxidation of a conjugated diolefin, such as butadiene—the catalyst was active and selective (87.9%) to the desired epoxidation product, 3,4-epoxy-1-butene, in this case. In the case of propylene, the simplest olefin containing an allylic ($CH_3$) hydrocarbon substituent and three allylic C—H bonds, performance was also as expected—good activity and very poor selectivity (2.6%) to the desired epoxidation product, propylene oxide, in this case.

Comparative Example 2

The same reactor system and a fresh sample of the catalyst used in Comparative Example 1 was used to evaluate catalytic activity for epoxidation of 1,5-hexadiene ($C_6H_{10}$), a non-conjugated diolefin. The 1,5-hexadiene was added to the feed stream as a vapor phase component. This was accomplished by using a thermostatted vapor-liquid equilibrium saturator that was swept with helium, an inert diluent. Thus, by proper selection of saturator temperature and flow rate of the helium sweep gas, known concentrations of 1,5-hexadiene vapor were added to the balance of the reactor feedstream to give a feed composition of 16% $C_6H_{10}$, 17% $O_2$, 67% n-butane, and 2 ppm 2-chlorobutane. At a reaction temperature of 200° C. and a gas hourly space velocity (GHSV) of 4300 $hr^{-1}$, the conversion of 1,5-hexadiene was 2.1% and the selectivity to epoxide product was 0%, with the only detected products being $CO_2$ and $H_2O$.

Example 1

The same catalyst charge and reactor system described in Comparative Example 1 was used for the epoxidation of isoprene, or 2-methyl-1,3-butadiene having the structure:

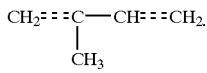

This molecule contains a —CH3 group, which is allylic to one of the two C=C double bonds. Based on the observed results in Comparative Examples 1 and 2, it would be expected that allylic C—H bond abstraction to occur, leading to poor selectivity to the olefin epoxide and complete combustion of all converted isoprene to $CO_2$ and $H_2O$.

At a reaction temperature of 205° C., a feed composition of 11.5% isoprene, 17% oxygen, 71.5% n-butane and 2 ppm 2-chlorobutane, a nd a feed rate of GHSV=6200 $hr^{-1}$, conversion of isoprene was 4.4% with a total selectivity to both isomers of isoprene monoepoxide equal to 57.7%. Based on the extreme non-selective conversion of both propylene and 1,5-hexadiene to their corresponding epoxides, the selective conversion of isoprene is unexpected, since isoprene contains an allylic —CH3 group, as do propylene and 1,5-hexadiene.

Epoxidation of isoprene can occur at two non-equivalent positions. Epoxidation at the $C_1=C_2$ double bond position of the molecule

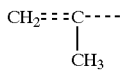

resembles propylene epoxidation since both species contain a —$CH_3$ group allylic to the C=C double bond. Epoxidation of isoprene at the $C_1=C_2$ position forms 3,4-epoxy-3-methyl-1-butene as the selective product. Based on the lack of selectivity for propylene epoxidation (Compative Example 1), one would not expect selectivity of this isomer to be higher than the 2.6% selectivity observed for propylene oxide. Epoxidation of isoprene at the $C_3=C_4$ double bond forms 3,4-epoxy-2-methyl-1-butene as the selective product. Epoxidation at this position resembles epoxidation of butadiene, since this C=C double bond is both conjugated and non-allylic. Thus, one should expect the selectivity of 3,4-epoxy-2-methyl-1-butene to be similar to that for 3,4-epoxy-1-butene formation. Accordingly, using this correlation, it is possible to calculate the selectivity for 3,4-epoxy-3-methyl-1-butene formation and compare this value with the selectivity for propylene oxide formation under similar conditions, making it possible to determine whether the conjugated double bond system of isoprene has actually enhanced the selectivity for epoxidation of C=C double bonds with attached allylic alkyl groups containing allylic C—H bonds.

The overall selectivity for both isomeric epoxides is 57.7%. The calculated selectivity for formation of 3,4-epoxy-3-methyl-1-butene compared to propylene, 22.2% vs. 2.6%, respectively, suggests that the presence of the conjugated double bond enhances the selectivity, even of the allylic epoxide product.

Example 2

The same catalyst charge and reactor system described in Comparative Example 1 was used for the epoxidation of piperylene (1,3-pentadiene) having the structure:

This molecule contains a —CH3 group, which is allylic to one of the two C=C double bonds. Based on the observed results in Comparative Examples 1 and 2, it would be expected that allylic C—H bond abstraction should occur preferentially, leading to essentially complete combustion of all converted piperylene to $CO_2$ and $H_2O$.

At a reaction temperature of 205° C., a feed composition of 11.5% piperylene, 17% oxygen, 71.5% n-butane and 2 ppm 2-chlorobutane, and a feed rate of GHSV=6200 $hr^{-1}$, conversion of piperylene was 4.1% with a total selectivity to both isomers of piperylene epoxide=48.7%. Based on the non-selective conversion of both propylene and 1,5-hexadiene to their corresponding epoxides, the selective conversion of piperylene is totally unexpected. Again, separation of the selectivities to each of the isomeric epoxides as described in Example 1, the selectivity for the formation of the allylic epoxide, 3,4-epoxy-1-pentene, is 15.1%, compared to propylene, which is 2.6%, under the same reaction conditions, suggesting that the presence of the conjugated double bond enhances the selectivity, even of the allylic epoxide product.

Examples 3–11

Various other promoted Ag catalysts were prepared, pretreated, and evaluated using the procedures and reactor described in Comparative Example 1. For the following examples, catalyst weights varied between 3.00 and 4.00 grams and overall flow rates of the different gas compositions gave gas hourly space velocities between 3100–6200 $hr^{-1}$. Catalyst performance data are summarized below in Table I. In each Example, the total selectivity to both isoprene monoepoxide isomers is much higher than would be expected, based on the selectivities observed for propylene oxide and hexadiene epoxide in Comparison Examples 1 and 2, respectively. These results also demonstrate that a wide range of promoters at different promoter loadings give selective performance for formation of isoprene monoepoxide isomers. The range of feed compositions used also show that selective formation of isoprene monoepoxide occurs for a wide range of olefin and oxygen concentrations. In Table I, the amount of the promoter refers to ppmw of promoter cation, e.g., $Cs^+$, Temp refers to the temperature (°C.) at which the experiment was carried out, the components of the feed gas are given in mole percent, Conv refers to conversion (%) and Select refers to selectivity (%), determined as described herein.

TABLE I

| Example No. | Promoter Salt | Amount | Temp | Feed Composition Oxygen | Isoprene | Butane | Conv | Select |
|---|---|---|---|---|---|---|---|---|
| 3 | CsCl | 810 | 200 | 17 | 12 | 71 | 1.9 | 54.4 |
| 4 | CsCl | 810 | 200 | 25 | 12 | 63 | 2.8 | 51.2 |
| 5 | CsCl | 937 | 210 | 17 | 12 | 71 | 2.4 | 61.9 |
| 6 | CsCl | 937 | 210 | 40 | 12 | 48 | 4.0 | 58.2 |
| 7 | CsCl | 586 | 210 | 17 | 12 | 71 | 4.1 | 52.3 |
| 8 | $CsNO_3$ | 893 | 210 | 17 | 12 | 71 | 4.6 | 59.1 |
| 9 | $CsNO_3$ | 210 | 210 | 25 | 12 | 63 | 5.1 | 58.0 |
| 10 | TlCl | 2000 | 210 | 17 | 12 | 71 | 4.9 | 38.2 |
| 11 | RbCl | 650 | 205 | 17 | 12 | 71 | 1.4 | 41.5 |

As in the case of Examples 1 and 2, the selectivities to each of the isoprene oxide isomers can be calculated separately. Thus, the selectivities to each of the isomeric monoepoxides were calculated for the monoepoxide product obtained in each of Examples 3, 5, 6, 8, and 9 and are set forth in Table II. The selectivity to the allylic epoxide, 3-methyl-3,4-epoxy-1-butene, varies from 14.5 to 21.0% for the various compositions and reaction conditions. In all cases, the selectivities are much higher than those for propylene and hexadiene in Comparative Examples 1 and 2, further illustrating the selectivity enhancing effects of the conjugated double bond system on epoxidation of conjugated olefins containing allylic C—H bonds.

TABLE II

| Example No. | Selectivity to 3-Methyl-3,4-Epopxy-1-Butene | Selectivity to 2-Methyl-3,4-Epoxy-1-Butene |
|---|---|---|
| 3 | 91.7 | 14.5 |
| 5 | 91.2 | 20.3 |
| 6 | 91.2 | 21.0 |
| 8 | 92.1 | 19.3 |
| 9 | 92.1 | 19.0 |

The invention has been described in detail with particular reference to preferred embodiments thereof, but it will be understood that variations and modifications may be effected within the spirit and scope of the invention.

We claim:

1. Process for the preparation of a monoepoxide of an olefin reactant having the formula:

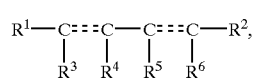

(I)

wherein $R^1$, $R^2$, $R^3$, $R^4$, $R^5$, and $R^6$ are independently selected from hydrogen, methyl, and $C_2$–$C_6$ linear or branched alkyl groups, provided that at least one $R^1$, $R^2$, $R^3$, $R^4$, $R^5$, and $R^6$ contains at least one C—H group that is allylic to one or both of the adjacent C=C double bonds, which comprises contacting in the vapor phase the olefin reactant with an oxygen-containing gas in the presence of a supported silver catalyst at epoxide-forming conditions of pressure and temperature, wherein the catalyst comprises a catalyst support material having a surface area of less than 10 square meters per gram having distributed on the surface thereof about 1 to 30 weight percent silver and about 10 to 5000 parts per million by weight (ppmw) of an epoxidation catalyst modifier selected from alkali earth metals, alkaline earth metals and thallium.

2. Process according to claim 1 wherein the olefin reactant and oxygen-containing gas are contacted in the gas phase at a temperature of about 175 to 250° C. and the catalyst comprises a catalyst support material having a surface area of less than 10 square meters per gram having distributed on the surface thereof about 2 to 25 weight percent silver and about 20 to 3000 parts per million by weight (ppmw) of the epoxidation catalyst modifier.

3. Process for the preparation of a monoepoxide of an olefin reactant having the formula:

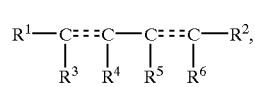

(I)

wherein $R^1$, $R^2$, $R^3$, $R^4$, $R^5$, and $R^6$ are independently selected from hydrogen, methyl, and $C_2$–$C_6$ linear or branched alkyl groups, provided that at least one $R^1$, $R^2$, $R^3$, $R^4$, $R^5$, and $R^6$ contains at least one C—H group that is allylic to one or both of the adjacent C=C double bonds and the olefin reactant contains 5 to 20 carbon atoms, which comprises contacting in the vapor phase at a temperature of about 175 to 250° C. a feed gas comprising (1) about 3 to 25 mole percent of the olefin reactant, (2) about 5 to 25 mole percent oxygen, (3) about 40 to 80 mole percent of a paraffin hydrocarbon containing 1 to 6 carbon atoms, (4) 20 to 500 ppmv ammonia and/or an amine, and (5) a total of about 0 to 10 mole percent of other components selected from water, carbon dioxide, argon and recycled epoxide product, with a supported silver catalyst comprising a catalyst support material having a surface area of less than 10 square meters per gram having distributed on the surface thereof about 2 to 25 weight percent silver and about 20 to 3000 parts per million by weight (ppmw) of an epoxidation catalyst modifier selected from alkali earth metals, alkaline earth metals and thallium.

4. Process according to claim 3 wherein the olefin reactant and oxygen-containing gas are contacted in the gas phase at a temperature of about 185 to 225° C. and the catalyst comprises a catalyst support material having a surface area of less than 10 square meters per gram having distributed on the surface thereof about 5 to 20 weight percent silver and about 50 to 1600 parts per million by weight (ppmw) of an epoxidation catalyst modifier selected from cesium, rubidium and thallium.

5. Process according to claim 4 wherein the olefin reactant is isoprene or piperylene.

* * * * *